US006586377B2

(12) United States Patent
Graham et al.

(10) Patent No.: US 6,586,377 B2
(45) **Date of Patent: *Jul. 1, 2003**

(54) CONTACT LENS CLEANING COMPOSITIONS

(75) Inventors: Richard Graham, Irvine, CA (US); Joseph G. Vehige, Laguna Niguel, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/005,638

(22) Filed: Dec. 3, 2001

(65) Prior Publication Data

US 2002/0065203 A1 May 30, 2002

Related U.S. Application Data

(63) Continuation of application No. 09/384,879, filed on Aug. 27, 1999, now abandoned, which is a continuation of application No. 08/979,730, filed on Nov. 26, 1997, now abandoned.

(51) Int. Cl.[7] .......................... C11D 1/722; C11D 3/48; A61K 31/55

(52) U.S. Cl. ...................... 510/112; 510/421; 510/424; 510/426; 510/473; 134/42; 422/28; 424/78.04

(58) Field of Search ................................ 510/112, 113, 510/473, 424, 421, 506, 426; 424/78.04; 134/42; 422/28

(56) References Cited

U.S. PATENT DOCUMENTS

| | | | | | |
|---|---|---|---|---|---|
| 3,311,577 | A | | 3/1967 | Rankin | 514/496 |
| 4,029,817 | A | | 6/1977 | Blanco et al. | 424/329 |
| 4,046,706 | A | | 9/1977 | Krezanoski | 252/106 |
| 4,323,467 | A | | 4/1982 | Fu | 252/106 |
| 4,510,065 | A | | 4/1985 | Sherman | 252/106 |
| 4,525,346 | A | | 6/1985 | Stark | 424/80 |
| 4,551,461 | A | | 11/1985 | Sherman | 514/275 |
| 4,581,374 | A | | 4/1986 | Nelson et al. | 514/574 |
| 4,758,595 | A | | 7/1988 | Ogunbiyi et al. | 514/635 |
| 4,783,488 | A | * | 11/1988 | Ogunbiyi et al. | 514/635 |
| 4,786,436 | A | | 11/1988 | Ogunbiyi et al. | 510/112 |
| 4,808,239 | A | * | 2/1989 | Schafer et al. | 134/42 |
| 4,880,601 | A | | 11/1989 | Andermann et al. | 422/28 |
| 4,904,698 | A | | 2/1990 | Adkins, Jr. et al. | 514/624 |
| 5,128,058 | A | | 7/1992 | Ishii et al. | 510/113 |
| 5,300,296 | A | | 4/1994 | Holly et al. | 424/427 |
| 5,322,667 | A | | 6/1994 | Sherman | 422/28 |
| 5,332,224 | A | | 7/1994 | Libit et al. | 514/63 |
| 5,380,303 | A | | 1/1995 | Holly et al. | 604/290 |
| 5,401,327 | A | | 3/1995 | Ellis et al. | 134/42 |
| 5,405,878 | A | | 4/1995 | Ellis et al. | 422/28 |
| 5,422,029 | A | | 6/1995 | Potini et al. | 252/106 |
| 5,422,073 | A | | 6/1995 | Mowrey-McKee et al. | 422/28 |
| 5,453,435 | A | | 9/1995 | Raheja et al. | 514/402 |
| 5,494,937 | A | | 2/1996 | Asgharian et al. | 514/772.3 |
| 5,500,141 | A | | 3/1996 | Kormann et al. | 252/174.15 |
| 5,500,144 | A | | 3/1996 | Potini et al. | 252/174.15 |
| 5,580,392 | A | | 12/1996 | Sulc et al. | 134/7 |
| 5,589,387 | A | | 12/1996 | Cafaro | 435/264 |
| 5,591,426 | A | | 1/1997 | Dabrowski et al. | 424/78.04 |
| 5,607,908 | A | | 3/1997 | Potini et al. | 510/115 |
| 5,624,958 | A | | 4/1997 | Isaacs et al. | 514/546 |
| 5,653,972 | A | | 8/1997 | Desai et al. | 424/28.04 |
| 5,654,262 | A | * | 8/1997 | Desai et al. | 510/115 |
| 5,719,110 | A | | 2/1998 | Cook | 510/112 |
| 5,765,579 | A | | 6/1998 | Heiler et al. | 514/635 |
| 5,773,396 | A | | 6/1998 | Zhang et al. | 510/115 |
| 5,800,807 | A | * | 9/1998 | Hu et al. | 424/78.04 |
| 6,037,328 | A | * | 3/2000 | Hu et al. | 514/23 |
| 6,063,745 | A | | 5/2000 | Graham et al. | 510/112 |
| 6,121,327 | A | * | 9/2000 | Tsuzuki et al. | 514/642 |
| 6,319,883 | B1 | * | 11/2001 | Graham et al. | 510/112 |

FOREIGN PATENT DOCUMENTS

| | | |
|---|---|---|
| GB | 1432345 | 4/1972 |
| GB | 1437345 | 4/1976 |
| WO | 9832421 | 7/1998 |

* cited by examiner

*Primary Examiner*—Lorna M. Douyon
(74) *Attorney, Agent, or Firm*—Pillsbury Winthrop LLP; Nicole S. Bradley; Peter Jon Gluck

(57) ABSTRACT

Solutions useful to clean contact lenses include a surfactant component in an effective amount; and a viscosity inducing component, preferably selected from cellulosic derivatives and more preferably hydroxypropylmethyl cellulose, in an effective amount. Such solutions, which may include one or more additional components, have substantial contact lens cleaning benefits which, ultimately, lead to ocular health advantages and avoidance of problems caused by contact lens wear.

16 Claims, No Drawings

CONTACT LENS CLEANING COMPOSITIONS

This application is a continuation of application Ser. No. 09/384,879, filed Aug. 27, 1999, now abandoned which, in turn, is a continuation of application Ser. No. 08/979,730, filed Nov. 26, 1997 now abandoned.

BACKGROUND OF THE INVENTION

The present invention relates to compositions for treating, for example, cleaning, disinfecting, soaking, conditioning and wetting contact lenses. More particularly, the invention relates to multi-purpose solutions useful in treating contact lenses, for example, for removing deposit material from contact lenses, for disinfecting contact lenses, for soaking, conditioning and/or wetting contact lenses and the like, which provide substantial contact lens treating, e.g., cleaning, benefits to the users of such solutions.

Contact lenses need to be periodically treated, for example, cleaned, disinfected, soaked and the like, on a regular basis because of the tendency for a variety of microbes and other materials to accumulate on the lenses and/or the need to provide the lenses in suitable condition for safe and comfortable wear.

Fu U.S. Pat. No. 4,323,467 discloses aqueous compositions combining poly(oxyethylene)-poly(oxypropylene) substituted ethylenediamine surfactants, certain cellulose-derived polymer viscosity builders, germicidal agents, tonicity agents, sequestering agents and water for treating rigid contact lenses. The Fu patent does not disclose the use of hydroxypropylmethyl cellulose (HPMC) or of any specific buffer.

British Patent 1,432,345 discloses a contact lens disinfecting composition including an ophthalmically acceptable biguanide in a total amount of from 0.0005% to 0.05% by weight. This British patent discloses that the solution preferably has a pH of from 5 to 8 and employs a phosphate buffer. The patent also discloses employing additional bactericides, certain cellulose-derived thickening agents and non-ionic surfactants, as well as disodium EDTA in concentrations of at least 0.1%. This patent does not disclose the use of HPMC.

Ogunbiyi et al U.S. Pat. No. 4,758,595 discloses an aqueous solution of a biguanide in an amount of 0.000001 to 0.0003 weight percent in combination with a borate buffer system, EDTA, and one or more surfactants. This U.S. Patent additionally discloses that certain cellulose-derived viscosity builders can be included.

Mowrey-McKee et al U.S. Pat. No. 5,422,073 discloses a contact lens care solution including tromethamine, chelating agents, PHMB, surfactants and certain cellulose-derived viscosity inducing agents. This patent does not specifically disclose the use of HPMC.

There continues to be a need to provide new contact lens treatment systems, for example, multi-purpose solutions, that provide one or more benefits, for example, more effective contact lens cleaning.

SUMMARY OF THE INVENTION

New compositions for treating contact lenses have been discovered. The present compositions, for example, contact lens cleaning aqueous solutions and multi-purpose aqueous solutions, include surfactant components in amounts effective in removing deposit material from a contact lens contacted with the composition, and effective amounts of viscosity inducing components, preferably HPMC in an amount in a range of about 0.05% to about 0.5% (w/v). The present HPMC-containing compositions preferably have increased or enhanced effectiveness in removing deposit material from contact lenses contacted with the compositions relative to similar compositions without the HPMC. These compositions are surprising and unexpected in view of the above-noted prior art which discloses the use of cellulose-derived viscosity building polymers other than HPMC. In addition, the present compositions preferably include antimicrobial components, in combination with buffers to provide desired antimicrobial activity and performance effectiveness.

The inclusion of one or more still other components in the present compositions is effective in providing additional beneficial properties to the compositions. The present compositions, in addition to being effective in cleaning contact lenses, preferably have a multitude of applications, for example, as disinfecting, soaking, wetting and conditioning compositions, for contact lens care. The present compositions promote regular and consistent contact lens care and, ultimately, lead to or facilitate better ocular health.

Any suitable, preferably ophthalmically acceptable, surfactant component which is effective in cleaning contact lenses may be employed. The surfactant component preferably is nonionic and, more preferably, is selected from 4-(1,1,3,3-tetramethylbutyl)phenol/poly(oxyethylene) polymers, poly(oxyethylene)-poly(oxypropylene) block copolymers and mixtures thereof.

Although any suitable, for example, ophthalmically acceptable, viscosity inducing or thickening agent may be included in the present compositions, the viscosity inducing component preferably is selected from cellulosic derivatives and mixtures thereof, and more preferably is HPMC. The viscosity inducing component preferably is present in an amount in the range of about 0.05% to about 0.5% (w/v). Without wishing to limit the invention to any particular theory of operation, it is believed that the presence of a viscosity inducing component at least assists in providing the present compositions with enhanced passive contact lens cleaning properties. Passive cleaning refers to the cleaning which occurs during soaking of a contact lens, without mechanical or enzymatic enhancement. In particular, it has unexpectedly been found that the present compositions with HPMC present are more effective in passive cleaning of contact lenses relative to similar compositions without HPMC. The present combinations of components, including such viscosity inducing components, are effective in providing the degree of enhanced contact lens cleaning described herein.

In one embodiment of the present invention, multi-purpose solutions for contact lens care are provided. Such solutions comprise an aqueous liquid medium; a non-oxidative antimicrobial component in an amount effective to disinfect a contact lens contacted with the solution; a surfactant in an amount effective in cleaning a contact lens contacted with the solution; a buffer component, preferably a phosphate buffer component in an amount effective in maintaining the pH of the solution within a physiologically acceptable range; a viscosity inducing component preferably HPMC, present in an effective amount; and a tonicity component in an amount effective in providing the desired tonicity to the solution.

The antimicrobial component may be any suitable, preferably ophthalmically acceptable, material effective to disinfect a contact lens contacted with the present solutions. In one embodiment, the antimicrobial component is non-oxidative. Preferably, the non-oxidative antimicrobial component is selected from biguanides, biguanides polymers, salts thereof and mixtures thereof, and is present in an amount in the range of about 0.1 ppm to about 3 ppm or less than 5 ppm (w/v). The preferred relatively reduced concentration of the antimicrobial component has been found to be very effective, in the present compositions, in disinfecting contact lenses contacted with the compositions, while at the same time promoting lens wearer/user comfort and acceptability.

Although any suitable, preferably ophthalmically acceptable, tonicity component may be employed, a very useful tonicity component is sodium chloride or a combination of sodium chloride and potassium chloride.

The present compositions preferably include an effective amount of a chelating component. Any suitable, preferably ophthalmically acceptable, chelating component may be included in the present compositions, although ethylenediaminetetraacetic acid (EDTA), salts thereof and mixtures thereof are particularly effective.

Various combinations of two or more of the above-noted components may be used in providing at least one of the benefits described herein. Therefore, each and every such combination is included within the scope of the present invention.

These and other aspects of the present invention are apparent in the following detailed description, examples and claims.

DETAILED DESCRIPTION OF THE INVENTION

The present invention is directed to solutions useful for cleaning contact lenses and to multi-purpose solutions useful for treating, for example, cleaning, disinfecting, soaking, rinsing, wetting, conditioning and the like, contact lenses. Any contact lenses, for example, conventional hard contact lenses, rigid gas permeable contact lenses and soft, hydrophilic or hydrogel, contact lenses, can be treated in accordance with the present invention.

The present compositions, preferably solutions, useful for cleaning a contact lens comprise an aqueous liquid medium, a surfactant component in an amount effective in removing deposit material from a contact lens contacted with the composition, and an effective amount of a viscosity inducing component, preferably HPMC in an amount in the range of about 0.05% to about 0.5% (w/v).

In one embodiment, the present compositions, preferably solutions, comprise a liquid aqueous medium; a non-oxidative antimicrobial component in the liquid aqueous medium in an amount effective to disinfect a contact lens contacted with the composition; a surfactant, preferably a nonionic surfactant, component in an amount effective in cleaning, or removing deposit material from, a contact lens contacted with the composition; a buffer component, for example, a phosphate buffer component, in an amount effective in maintaining the pH of the composition within a physiologically acceptable range; an effective amount of a viscosity inducing component, preferably HPMC; and an effective amount of a tonicity component.

The present compositions preferably include an effective amount of a chelating or sequestering component, more preferably in a range of less than 0.1% (w/v). Each of the components, in the concentration employed, included in the compositions and the formulated compositions of the present invention preferably are ophthalmically acceptable. In addition, each of the components, in the concentration employed, included in the present compositions preferably is soluble in the liquid aqueous medium.

A composition or component thereof is "ophthalmically acceptable" when it is compatible with ocular tissue, that is, it does not cause significant or undue detrimental effects when brought into contact with ocular tissue. Preferably, each component of the present compositions is also compatible with the other components of the present compositions.

The surfactant component is present in an amount effective in cleaning, that is to at least facilitate removing, and preferably effective to remove, debris or deposit material from, a contact lens contacted with the surfactant-containing solution. Exemplary surfactant components include, but are not limited to, nonionic surfactants, for example, polysorbates (such as polysorbate 20—Trademark Tween 20), 4-(1,1,3,3-tetramethylbutyl) phenol polymers (such as the polymer sold under the trademark Tyloxapol), poly(oxyethylene)-poly(oxypropylene) block copolymers, glycolic esters of fatty acids, alkyl ether sulfates and the like, and mixtures thereof.

The surfactant component more preferably is nonionic, and still more preferably is selected from 4-(1,1,3,3-tetrabutyl)phenol/poly(oxyethylene) polymers, poly(oxyethylene)-poly(oxypropylene) block copolymers and mixtures thereof. Such block copolymers can be obtained commercially from the BASF Corporation under the trademark Pluronic®, and can be generally described as polyoxyethylene/polyoxypropylene condensation polymers terminated in primary hydroxyl groups. They may be synthesized by first creating a hydrophobe of desired molecular weight by the controlled addition of propylene oxide to the two hydroxyl groups of propylene glycol. In the second step of the synthesis, ethylene oxide is added to sandwich this hydrophobe between hydrophile groups.

In accordance with a more preferred embodiment of the invention, such block copolymers having molecular weights in the range of about 2500 to 13,000 daltons are suitable, with a molecular weight range of about 6000 to about 12,000 daltons being still more preferred. Specific examples of surfactants which are satisfactory include: poloxamer 108, poloxamer 188, poloxamer 237, poloxamer 238, poloxamer 288, poloxamer 407.

The amount of surfactant component present varies over a wide range depending on a number of factors, for example, the specific surfactant or surfactants being used, the other components in the composition and the like. Often the amount of surfactant is in the range of about 0.005% or about 0.01% to about 0.1% or about 0.5% or about 0.8% (w/v).

The viscosity inducing component is effective to enhance and/or prolong the cleaning and wetting activity of the surfactant component and/or condition the lens surface rendering it more hydrophilic (less lipophilic) and/or to act as a demulcent on the eye. Increasing the solution viscosity provides a film on the lens which may facilitate comfortable wearing of the treated contact lens. The viscosity inducing component may also act to cushion the impact on the eye surface during insertion and serves also to alleviate eye irritation.

Suitable viscosity inducing components include, but are not limited to, water soluble natural gums, cellulose-derived polymers and the like. Useful natural gums include guar gum, gum tragacanth and the like. Useful cellulose-derived viscosity inducing components include cellulose-derived polymers, such as hydroxypropyl cellulose, HPMC, carboxymethyl cellulose, methyl cellulose, hydroxyethyl cellulose and the like. More preferably, the viscosity inducing agent is selected from cellulose derivatives (polymers) and mixtures thereof.

A very useful viscosity inducing component is HPMC. The viscosity inducing component, and in particular HPMC, has been found to enhance the ability of the present compositions in cleaning, for example, in passively cleaning (e.g., without manual rubbing), contact lenses.

The viscosity inducing component is used in an amount effective to increase the viscosity of the solution, preferably to a viscosity in the range of about 1.5 to about 30, or even as high as about 750, cps at 25° C., preferably as determined by USP test method No. 911 (USP 23, 1995). The amount of viscosity inducing component preferably is in the range of about 0.01% to about 5% (w/v), with amounts of about 0.05% to about 0.5% being more preferred.

The present compositions preferably further comprise effective amounts of one or more additional components, such as an antimicrobial component; a buffer component; a chelating or sequestering component; a tonicity component; and the like and mixtures thereof. The additional component or components may be selected from materials which are known to be useful in contact lens care compositions and are included in amounts effective to provide the desired effect or benefit. When an additional component is included, it is preferably compatible under typical use and storage conditions with the other components of the composition. For instance, the aforesaid additional component or components preferably are substantially stable in the presence of the surfactant and viscosity inducing components described herein.

The presently useful antimicrobial components include chemicals which derive their antimicrobial activity through a chemical or physiochemical interaction with microbes or microorganisms, such as those contaminating a contact lens. Suitable antimicrobial components are those generally employed in ophthalmic applications and include, but are not limited to, quaternary ammonium salts used in ophthalmic applications such as poly[dimethylimino-2-butene-1,4-diyl] chloride, alpha-[4-tris(2-hydroxyethyl) ammonium]-dichloride (chemical registry number 75345-27-6, available under the trademark Polyquaternium 1® from Onyx Corporation), tromethamine, benzalkonium halides, and biguanides, such as salts of alexidine, alexidine-free base, salts of chlorhexidine, hexamethylene biguanides and their polymers, and salts thereof, antimicrobial polypeptides, chlorine dioxide precursors, and the like and mixtures thereof. Generally, the hexamethylene biguanide polymers (PHMB), also referred to as polyaminopropyl biguanide (PAPB), have molecular weights of up to about 100,000. Such biguanide polymers are known and are disclosed in Ogunbiyi et al U.S. Pat. No. 4,758,595, the disclosure of which is hereby incorporated in its entirety by reference herein.

The antimicrobial components useful in the present invention preferably are present in the liquid aqueous medium in concentrations in the range of about 0.00001% to about 2% (w/v).

More preferably, the antimicrobial component is present in the liquid aqueous medium at an ophthalmically acceptable or safe concentration such that the user can remove the disinfected lens from the liquid aqueous medium and thereafter directly place the lens in the eye of safe and comfortable wear.

The antimicrobial components suitable for inclusion in the present invention include chlorine dioxide precursors. Specific examples of chlorine dioxide precursors include stabilized chlorine dioxide (SCD), metal chlorites, such as alkali metal and alkaline earth metal chlorites, and the like and mixtures thereof. Technical grade sodium chlorite is a very useful chlorine dioxide precursor. Chlorine dioxide-containing complexes, such as complexes of chlorine dioxide with carbonate, chlorine dioxide with bicarbonate and mixtures thereof are also included as chlorine dioxide precursors. The exact chemical composition of many chlorine dioxide precursors, for example, SCD and the chlorine dioxide complexes, is not completely understood. The manufacture or production of certain chlorine dioxide precursors is described in McNicholas U.S. Pat. No. 3,278,447, which is incorporated in its entirety herein by reference. Specific examples of useful SCD products include that sold under the trademark Dura Klor by Rio Linda Chemical Company, Inc., and that sold under the trademark Anthium Dioxide by International Dioxide, Inc.

If a chlorine dioxide precursor is included in the present compositions, it preferably is present in an effective contact lens disinfecting amount. Such effective disinfecting concentrations preferably are in the range of about 0.002 to about 0.06% (w/v) of the present compositions. Such chlorine dioxide precursors may be used in combination with other antimicrobial components, such as biguanides, biguanide polymers, slats thereof and mixtures thereof.

In the event that chlorine dioxide precursors are employed as antimicrobial components, the compositions preferably have an osmolality of at least about 200 mOsmol/kg and are buffered to maintain the pH within an acceptable physiological range, for example, a range of about 6 to about 10.

It has been found that reduced amounts of non-oxidative antimicrobial components, for example, in a range of about 0.1 ppm to about 3 ppm or less than 5 ppm (w/v), in the present compositions are effective in disinfecting contact lenses and reduce the risk of such antimicrobial components causing ocular discomfort and/or irritation. Such reduced concentration of antimicrobial component is very useful when the antimicrobial component employed is selected from biguanides, biguanide polymers, salts thereof and mixtures thereof.

When a contact lens is desired to be disinfected by the present compositions, an amount of the antimicrobial component effective to disinfect the lens is used. Preferably, such an effective amount of the antimicrobial component reduces the microbial burden or load on the contact lens by one log order in three hours. More preferably, an effective amount of the disinfectant reduces the microbial load by one log order in one hour.

The buffer component is present in an amount effective to maintain the pH of the composition or solution in the desired range, for example, in a physiologically acceptable range of about 4 or about 5 or about 6 to about 8 or about 9 or about 10. In particular, the solution preferably has a pH in the range of about 6 to about 8. Any material which is ophthalmically acceptable and has buffering effectiveness in the present applications may be employed. Such buffers may include organic materials, such as tromethamine and the like, inorganic materials, such as phosphates, borates carbonates and the like, and mixtures thereof. Particularly useful phosphate buffer components include one or more phosphate buffers, for example, combinations of monobasic phosphates, dibasic phosphates and the like, such as those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$) and potassium monobasic phosphate ($KH_2PO_4$). The present buffer components frequently are used in amounts in a range of about 0.01% or about 0.02% to about 1% or about 2% (w/v) or more.

A chelating or sequestering component preferably is included in an amount effective to enhance the effectiveness of the antimicrobial component and/or to complex with metal ions to provide more effective cleaning of the contact lens.

A wide range of organic acids, amines or compounds which include an acid group and an amine function are capable of acting as chelating components in the present compositions. For example, nitrilotriacetic acid, diethylenetriaminepentacetic acid, hydroxyethylethylenediaminetriacetic acid, 1,2-diaminocyclohexane tetraacetic acid, hydroxyethylaminodiacetic acid, ethylenediaminetetraacetic acid and its salts, polyphosphates, citric acid and its salts, tartaric acid and its salts, and the like and mixtures thereof, are useful as chelating components. Ethylenediaminetetraacetic acid (EDTA) and its alkali metal salts, are preferred, with disodium salt of EDTA, also known as disodium edetate, being particularly preferred.

The chelating component preferably is present in an effective amount, for example, in a range of about 0.01% and about 1% (w/v) of the solution.

In a very useful embodiment, particularly when the chelating component is EDTA, salts thereof and mixtures thereof, a reduced amount is employed, for example, in the range of less than about 0.1% (w/v). Such reduced amounts of chelating component have been found to be effective in the present compositions while, at the same time, providing for reduced discomfort and/or ocular irritation.

The liquid aqueous medium used is selected to have no substantial deleterious effect on the lens being treated, or on the wearer of the treated lens. The liquid medium is constituted to permit, and even facilitate, the lens treatment or treatments by the present compositions. The liquid aqueous medium advantageously has an osmolality in the range of at least about 200 mOsmol/kg for example, about 300 or about 350 to about 400 mOsmol/kg. The liquid aqueous medium more preferably is substantially isotonic or hypertonic (for example, slightly hypertonic) and/or is ophthalmically acceptable.

The liquid aqueous medium preferably includes an effective amount of a tonicity component to provide the liquid medium with the desired tonicity. Such tonicity components may be present in the liquid aqueous medium and/or may be introduced into the liquid aqueous medium. Among the suitable tonicity adjusting components that may be employed are those conventionally used in contact lens care products, such as various inorganic salts. Sodium chloride and/or potassium chloride and the like are very useful tonicity components. The amount of tonicity component included is effective to provide the desired degree of tonicity to the solution. Such amount may, for example, be in the range of about 0.4% to about 1.5% (w/v). If a combination of sodium chloride and potassium chloride is employed, it is preferred that the weight ratio of sodium chloride to potassium chloride be in the range of about 3 to about 6 or about 8.

Methods for treating a contact lens using the herein described compositions are included within the scope of the invention. Such methods comprise contacting a contact lens with such a composition at conditions effective to provide the desired treatment to the contact lens.

The contacting temperature is preferred to be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs at or about atmospheric pressure. The contacting preferably occurs for a time in the range of about 5 minutes or about 1 hour to about 12 hours or more.

The contact lens can be contacted with the liquid aqueous medium by immersing the lens in the medium. During at least a portion of the contacting, the liquid medium containing the contact lens can be agitated, for example, by shaking the container containing the liquid aqueous medium and contact lens, to at least facilitate removal of deposit material from the lens. After such contacting step, the contact lens may be manually rubbed to remove further deposit material from the lens. The cleaning method can also include rinsing the lens substantially free of the liquid aqueous medium prior to returning the lens to a wearers eye.

The following non-limiting examples illustrate certain aspects of the present invention.

EXAMPLE 1

A solution is prepared by blending together the following components:

| | |
|---|---|
| PHMB (polyhexamethylene biguanide) | 1 ppm (w/v) |
| Disodium EDTA | 0.05% (w/v) |
| Tyloxapol | 0.025% (w/v) |
| Tromethamine | 1.2% (w/v) |
| HPMC (Hydroxypropylmethyl Cellulose) | 0.15% (w/v) |
| Sodium Chloride | 0.37% (w/v) |
| Water (USP) | Q.S. 100% |
| pH (adjusted with HCl) | 7.5 |

Approximately three (3) ml of this solution is introduced into a lens vial containing a lipid, oily deposit laden, hydrophilic or soft contact lens. The contact lens is maintained in this solution at room temperature for at least about four (4) hours. This treatment is effective to disinfect the contact lens. In addition, it is found that a substantial portion of the deposits previously present on the lens has been removed. This demonstrates that this solution has substantial passive contact lens cleaning ability.

After this time, the lens is removed from the solution and is placed in the lens wearer's eye for safe and comfortable wear. Alternately, after the lens is removed from the solution, it is rinsed with another quantity of this solution and the rinsed lens is then placed in the lens wearer's eye for safe and comfortable wear.

EXAMPLE 2

Example 1 is repeated except that the lens is rubbed and rinsed with a different quantity of the solution prior to being placed in the lens vial. After at least about four (4) hours, the lens is removed from the solution. The lens is then placed in the lens wearer's eye for safe and comfortable wear.

EXAMPLE 3

The solution of Example 1 is used as a long-term soaking medium for a hydrophilic contact lens. Thus, approximately three (3) ml of this solution is placed in a vial and a contact lens is maintained in the solution at room temperature for about sixty (60) hours. After this soaking period, the lens is removed from the solution and placed in the lens wearer's eye for safe and comfortable wear. Alternately, after the lens is removed from the solution, it is rinsed with another quantity of this solution and the rinsed lens is then placed in the lens wearer's eye for safe and comfortable wear.

EXAMPLE 4

A hydrophilic contact lens is ready for wear. In order to facilitate such wearing, one or two drops of the solution of Example 1 is placed on the lens immediately prior to placing the lens in the lens wearer's eye. The wearing of this lens is comfortable and safe.

EXAMPLE 5

A lens wearer wearing a contact lens applies one or two drops of the solution of Example 1 in the eye wearing the lens. This effects a re-wetting of the lens and provides for comfortable and safe lens wear.

EXAMPLE 6

A series of tests are conducted to evaluate the passive contact lens cleaning ability of the solution prepared in accordance with Example 1 compared to other solutions.

The first of these other solutions, referred to hereinafter as Composition A, is similar to the solution prepared in accordance with Example 1 except no HPMC is included.

The second of these other solutions, referred to hereinafter as Composition B, is sold under the trademark ReNu® by Bausch & Lomb and includes 0.5 ppm PHMB, a poly (oxyethylene)-poly(oxypropylene) substituted ethylenediamine surfactant, a borate buffer system, 0.1% disodium EDTA, and sodium chloride as a tonicity agent.

The remaining other solutions are as follows:

Composition C is sold by Alcon under the trademark Opti-Free™

Composition D is sold by Ciba Vision Care under the trademark Solo Care™soft

Composition E a saline solution sold by Allergen under the trademark Lens Plus™

Each of these compositions is tested to evaluate its passive cleaning ability, specifically its ability to passively remove lipid-containing soil from a contact lens.

These tests are conducted as follows. A model lipid soil is prepared by combining one part by weight of Apiezon AP 101, 1.38 parts by weight paraffin oil and 0.01 parts by weight of Oil Red O. A red grease mixture is produced. This soil is deposited by first coating a circular stamp device with a diameter of about ½ inch which is plugged with cotton. The coated device is then stamped on the bottom of a tissue culture well made of polystyrene making sure that a light uniform coat is deposited on the bottom surface. Three (3) wells are coated for each solution to be tested. Two (2) sets of the coated wells are prepared. One set for one hour soaking and the second set for four (4) hours soaking. The coated wells are photographed in a photocopy machine and marked as the initial point.

The plates are cleaned as follows. 10 ml of each of the cleaning solutions is pipetted into the freshly prepared coated wells. One set of wells is allowed to soak for one hour and the second set is allowed to soak for four (4) hours. After the soaking cycle, the solution is decanted by flipping the well upside down.

Visual observations of any changes in the coating are made during the soaking cycle. At the end of the soaking cycle the wells are again photographed in a photocopy machine.

The estimated passive cleaning resulting from the soaking is ranked 1 to 5 with 1 representing the highest degree of passive cleaning and 5 representing the lowest degree of passive cleaning. The results of this ranking are as follows.

| Solution | 1 hr. Soaking | 4 hrs. Soaking | Average Rank |
|---|---|---|---|
| Example 1 | 1 | 1 | 1 |
| Composition A | 2 | 2 | 2 |
| Composition B | 4 | 4 | 4 |
| Composition C | 5 | 5 | 5 |
| Composition D | 3 | 3 | 3 |
| Composition E | 5 | 5 | 5 |

After the one (1) hour soak, dispersion and solubilization of some of the lipid substance is observed in the wells soaked with the solution in accordance with Example 1, Composition A and Composition D. Strings of the coating start to roll up and are seen floating on the surface of the solution. These results are seen again after the four (4) hour soak.

These results indicate that the solution in accordance with Example 1 is the most effective in passive cleaning regimens both in the one (1) hour and four (4) hours soaking. Visual observations show the effectiveness rankings of the Example 1 solution and Compositions A and B to be: Example 1> Composition A>> Composition B. Composition C is the least efficacious of the solutions, its lipid cleaning efficacy comparable only to the saline solution, Composition E. Composition A, on the other hand, shows more cleaning after the four (4) hours soaking period, while after one (1) hour soaking showing only the beginnings of dispersion of the coating. Composition D is a more effective passive cleaner than is Composition B.

When comparing the solution in accordance with Example 1 with Composition A, it is seen that the inclusion of HPMC in the solution of Example 1, in combination with the other ingredients present, provides an enhancement in passive cleaning efficacy.

While this invention has been described with respect to various specific examples and embodiments, it is to be understood that the invention is not limited thereto and that it can be variously practiced within the scope of the following claims.

What is claimed is:

1. A multi-purpose aqueous liquid contact lens care composition consisting of:

a non-oxidative antimicrobial component in an amount of less than 5 ppm, said amount of non-oxidative antimicrobial being effective to disinfect a contact lens contacted with said composition, a surfactant component in an amount from about 0.005% to about 0.8% (w/v), said amount of surfactant being effective in removing deposit material from a contact lens contacted in said composition, and hydroxypropylmethyl cellulose as a viscosity inducing component in an amount from about 0.05% to 0.5% (w/v), said amount of hydroxypropylmethyl cellulose being effective to increase the viscosity of said composition and to enhance the effectiveness of said composition in passively removing deposit material from the contact lens during said contacting, said composition having a viscosity in a range of about 1.5 cps to about 30 cps.

2. The multi-purpose aqueous liquid contact lens care composition of claim 1 wherein said antimicrobial component is selected from the group consisting of biguanides, biguanide polymers, salts thereof and mixtures thereof.

3. The multi-purpose aqueous liquid contact lens care composition of claim 1 wherein said surfactant component is selected from the group consisting of nonionic surfactants and mixtures thereof.

4. The multi-purpose aqueous liquid contact lens care composition of claim 1 wherein said surfactant component is selected from the group consisting of polysorbates, 4-(1,1,3,3-tetramethylbutyl) phenol/poly(oxyethylene) polymers, poly(oxyethylene)-poly(oxypropylene) block copolymers, glycolic esters of fatty acids, alkyl ether sulfates and mixtures thereof.

5. A method for cleaning a contact lens consisting essentially of:

soaking a contact lens laden with deposit material in a composition having a viscosity in a range of about 1.5 cps to about 30 cps, the composition comprising an aqueous liquid medium, a non-oxidative antimicrobial component in an amount of less than 5 ppm, said amount of non-oxidative antimicrobial being effective to disinfect a contact lens soaked in said composition and hydroxypropylmethyl cellulose as a viscosity inducing component in an amount from about 0.05% to 0.5% (w/v), said amount of hydroxypropylmethyl cellulose being effective to increase the viscosity of said composition and to enhance the effectiveness of said composition in passively removing deposit material from the contact lens during soaking of said contact lens laden with deposit material in said composition; and inserting said soaked contact lens into a user's eye.

6. The method of claim 5 wherein said antimicrobial component is selected from the group consisting of biguanides, biguanide polymers, salts thereof and mixtures thereof.

7. The method of claim 5 wherein said composition further includes an effective amount of a chelating component.

8. The method of claim 5 wherein said composition further includes a surfactant component in an amount from about 0.005% to about 0.8% (w/v), said amount of surfactant being effective in removing deposit material from a contact lens soaked in said composition.

9. The method of claim 8 wherein said surfactant component is selected from the group consisting of nonionic surfactants and mixtures thereof.

10. The method of claim 8 wherein said surfactant component is selected from the group consisting of polysorbates, 4-(1,1,3,3,-tetramethylbutyl) phenol/poly(oxyethylene) polymers, poly(oxyethylene)-poly(oxypropylene) block copolymers, glycolic esters of fatty acids, alkyl ether sulfates and mixtures thereof.

11. A method for cleaning a contact lens consisting essentially of:

soaking a contact lens laden with deposit material in a composition having a viscosity in a range of about 1.5 cps to about 30 cps, the composition comprising an aqueous liquid medium, a non-oxidative antimicrobial component in an amount of less than 5 ppm, said amount of non-oxidative antimicrobial being effective to disinfect a contact lens soaked in said composition and hydroxypropylmethyl cellulose as a viscosity inducing component in an amount from about 0.05% to 0.5% (w/v), said amount of hydroxypropylmethyl cellulose being effective to increase the viscosity of said composition and to enhance the effectiveness of said composition in passively removing deposit material from the contact lens during soaking of said contact lens laden with deposit material in said composition;

rinsing said soaked contact lens with said composition; and inserting said soaked contact lens into a user's eye.

12. The method of claim 11 wherein said antimicrobial component is selected from the group consisting of biguanides, biguanide polymers, salts thereof and mixtures thereof.

13. The method of claim 11 wherein said composition further includes an effective amount of a chelating component.

14. The method of claim 11 wherein said composition further includes a surfactant component in an amount from about 0.005% to about 0.8% said amount of surfactant being effective in removing deposit material from a contact lens soaked in said composition.

15. The method of claim 14 wherein said surfactant component is selected from the group consisting of nonionic surfactants and mixtures thereof.

16. The method of claim 14 wherein said surfactant component is selected from the group consisting of polysorbates, 4-(1,1,3,3,-tetramethylbutyl) phenol/poly(oxyethylene) polymers, poly(oxyethylene)-poly(oxypropylene) block copolymers, glycolic esters of fatty acids, alkyl ether sulfates and mixtures thereof.

* * * * *